United States Patent [19]

Heath

[11] Patent Number: 4,737,168

[45] Date of Patent: Apr. 12, 1988

[54] SOLIDS SEPARATION SYSTEM FOR NATURAL GAS WELLS

[75] Inventor: Rodney T. Heath, Farmington, N. Mex.

[73] Assignee: U.S. Enertek, Inc., Farmington, N. Mex.

[21] Appl. No.: 76,335

[22] Filed: Jul. 22, 1987

[51] Int. Cl.⁴ .............................................. B01D 19/00
[52] U.S. Cl. .......................................... 55/45; 55/52; 55/165; 55/176
[58] Field of Search ................. 55/36, 45, 52, 55, 164, 55/165, 171–177

[56] References Cited

U.S. PATENT DOCUMENTS

| Re. 19,666 | 8/1935 | McMurray | 55/45 |
| 1,513,294 | 10/1924 | Stigau | 55/172 X |
| 2,995,202 | 8/1961 | Mlasgow | 55/45 |
| 3,273,318 | 9/1966 | Meyer | 55/175 |
| 4,017,275 | 4/1977 | Hodgson | 55/177 X |

Primary Examiner—Charles Hart
Attorney, Agent, or Firm—Klaas & Law

[57] ABSTRACT

A separator system for separating gas, solids, and water issuing as effluent from a wellhead of a natural gas well. The system comprises an elongated tank means for mounting in a vertical attitude; a gas collection and dispersion means disposed within the tank means to effectuate upward ascent of collected gas; a solids collection means fed by gravitational separation; control gas monitor and control means to operatively monitor and control system operation; and a gas outlet means.

16 Claims, 2 Drawing Sheets

SOLIDS SEPARATION SYSTEM FOR NATURAL GAS WELLS

BACKGROUND OF THE INVENTION

The present invention relates generally to separator apparatus employed for processing natural gas wellhead effluent, and in particular, to a separator system which will separate solids such as coal, gas and water at the wellhead site.

When processing natural gas at the wellhead site to produce sales gas, it is conventional practice to provide a system for separation of water and hydrocarbons which may include conventional high or low pressure separator apparatus as generally described in my prior U.S. Pat. Nos. 4,579 565 and 4,198,214 the disclosures of which are incorporated herein by reference. In general, such separator apparatus comprises a horizontal vessel having a gas-operated heater associated with a fire tube located in the vessel to provide heat and pressure during the separation process whereby light end hydrocarbons are separated from heavy end hydrocarbons and water to produce sales gas. Such apparatus and systems are designed to be continuously operable at the wellhead site without the necessity for the presence of operator personnel and are intended to be continuously operable by use of self-generated supply gas used for heater fuel and for operation of controls.

In some situations, such as a natural gas well located in a coal field, the wellhead effluent may contain relatively large amounts of water and solid materials such as coal pieces, particles and dust, which can cause problems in production of sales gas and also create environmental problems in connection with disposal of waste material.

A primary object of the present invention is to provide continuously operable separator apparatus which will separate gas, water and solids such as coal in wellhead effluent at the wellhead site in an efficient low cost manner.

Another object of the invention is to provide separator apparatus which will be non-polluting in operation, prevent loss of gas, and enable recovery of the solids.

These and other objects will become apparent throughout the following description of the invention.

SUMMARY OF THE INVENTION

In general, the system of the present invention comprises an elongated cylindrical separator tank means mounted in a vertical attitude for receiving relatively high pressure (e.g. 100 to 1000 or more psig) wellhead effluent. Liquids are collected in a lower portion of the separator tank means and gas is collected in an upper portion thereof. Liquids and solids are removed through a bottom portion of the tank means. A vertically disposed cylindrical elongated hood means of relatively small diameter, less than the inside diameter of the tank means, is coaxially mounted within a lower portion of the tank means containing the wellhead effluent liquids so as to be surrounded by the liquids and enable upward flow of gas bubbles between the outer wall of the hood means and the inside wall of the tank means. The hood means has an effluent inlet means located between a closed top end portion and an open bottom end portion to initially separate the gas from the liquids and solids and create a pocket of trapped gas therein. A relatively large diameter cap means is coaxially mounted on the top end portion of the hood means to provide a gas trap chamber for upwardly flowing gas bubbles and a relatively narrow width annular flow channel between the side wall of the tank means and the cap means and also to provide a gas trap means adjacent to the flow channel. The hood means may include a plurality of outwardly and downwardly extending gas discharge scrubber means in communication with the gas pocket in the interior of the hood means to enable downward gas discharge into the liquids surrounding the hood means to cause downward flow of fine solid particles relative thereto. A solids collection means is mounted below the hood means and has a slurry discharge outlet means leading therefrom for removal of the solids in a liquid slurry. A mist extraction means is situated in the upper portion of the tank means to entrain liquid droplets prior to discharge of gas through a gas outlet means at the top of the tank means.

BRIEF DESCRIPTION OF THE DRAWINGS

An illustrative and presently preferred embodiment of the invention is shown in the accompanying drawing wherein.

DETAILED DESCRIPTION OF A PREFERRED EMBODIMENT

Figure 1:
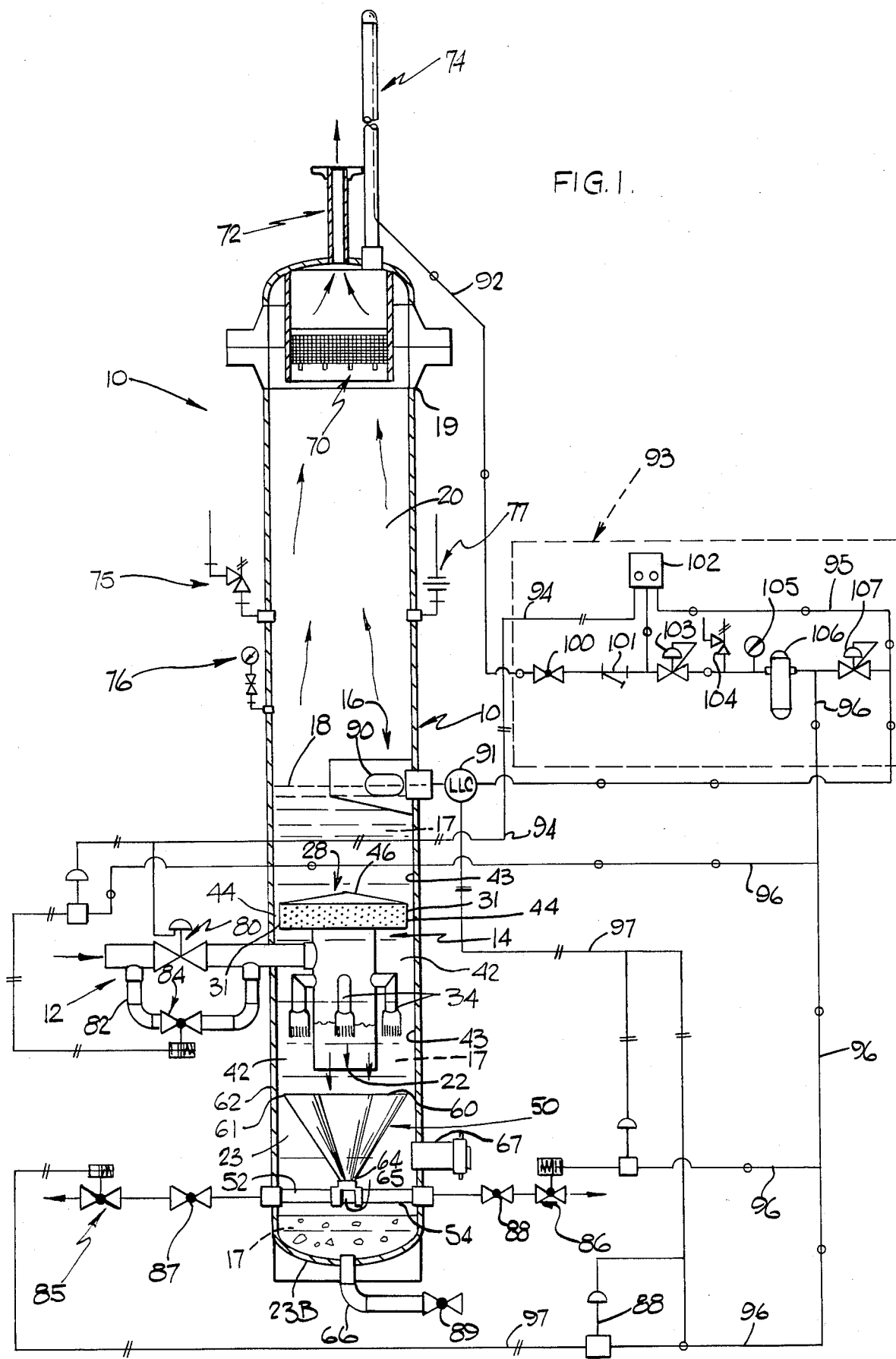
FIG. 1 is an elevational schematic view partially in section showing a separator apparatus.

In general, the present invention comprises an elongated cylindrical tank means 10 as shown in FIG. 1 mounted in a vertical attitude for receiving natural gas wellhead effluent containing water and/or liquid hydrocarbons and solids, such as coal particles, through an inlet means 12 and a centrally located cylindrical hood means 14. A conventional liquid level control means 16 is provided in an intermediate portion of tank means 10 for maintaining a body of water and other liquids 17 in the tank means 10 at a level 18 above the hood means 14 and below the upper end portion 19 of the tank means 10 and to provide an elongated gas collection chamber 20 in the upper portion of tank means 10.

Figure 2:
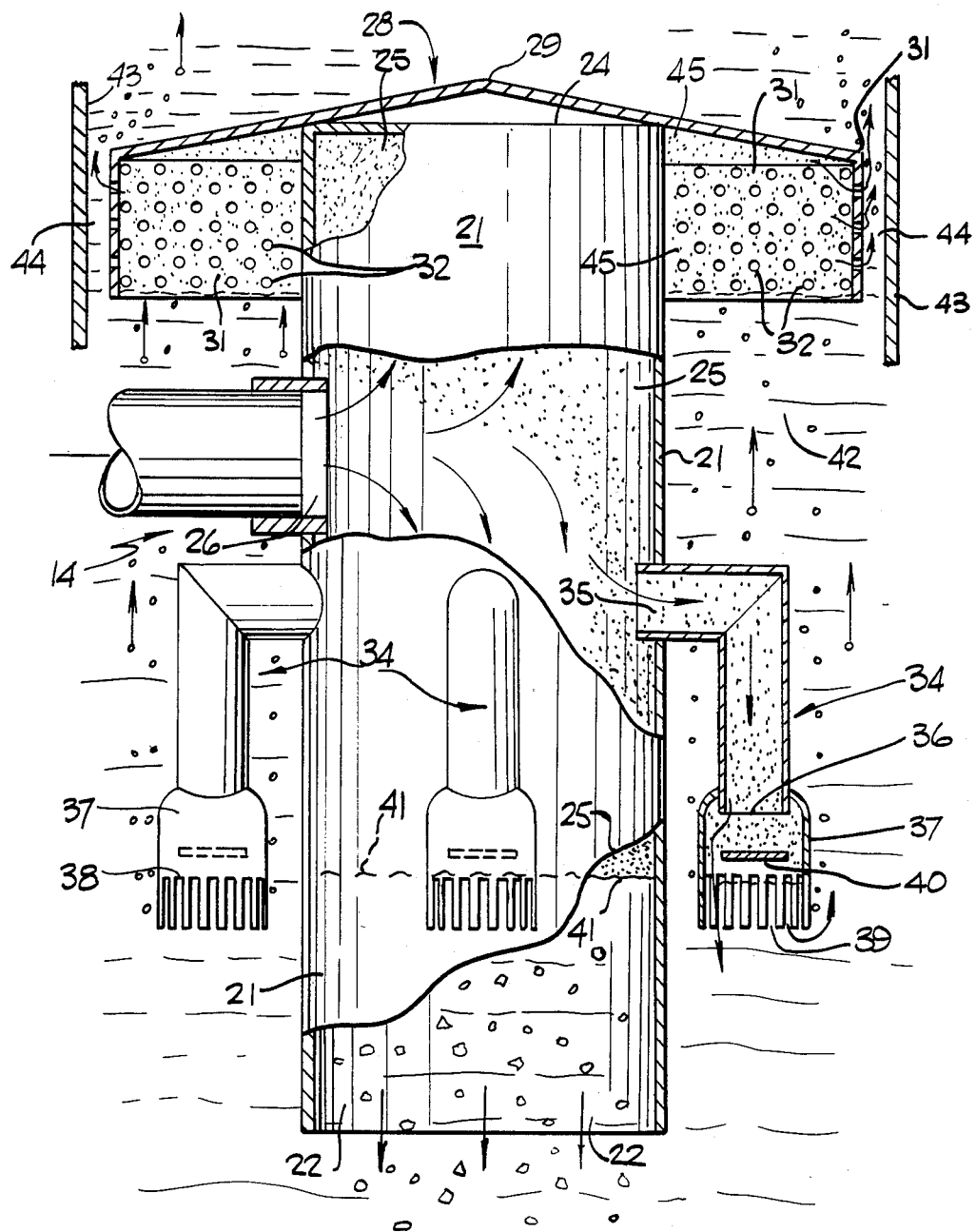
FIG. 2 is an enlarged elevational view of a hood means with bubble column means and gas dispersion means.

Hood means 14, as shown in Figs. 1 and 2, comprises an elongated cylindrical member 21 having an open bottom end portion 22 for discharging the water and solids portion of the well effluent into a lower portion 23 of tank means 10 at a location spaced upwardly a substantial distance from the bottom 23B of tank means 10. Hood means 14 also has a closed upper end portion 24 providing a closed chamber 25 above inlet opening 26. A baffle and gas trap mean 28 is mounted on the upper end portion of hood means 14 for collecting upwardly moving gas bubbles in the liquid and radially discharging collected gas back into the liquid in a narrow width channel between the baffle and gas trap means 28 and the side wall of the separator tank means 10. Baffle and gas trap means 28 comprise a conical cap member 29 having a diameter substantially larger than the diameter of cylindrical member 21 fixed to the upper end portion 24 of hood means 14 and an annular side wall member 31 having a plurality of circumferentially spaced circular gas discharge openings 32. A plurality of circumferentially spaced gas discharge means 34 are mounted on the outer periphery of hood means 14 with radially outwardly extending gas inlet openings 35 connected to gas collection chamber 25. Downwardly facing gas discharge openings 36 are located in an enlarged diameter discharge member 37 having a plurality of circumferentially spaced gas discharge slots 38 and a cylindrical gas discharge opening 39 at the lower end portion thereof. A baffle plate 40 may be centrally mounted in member 37 to cause flow of gas thereabout.

In normal continuous operation, the natural gas wellhead effluent is discharged at wellhead pressure, e.g. 1000 psig, into hood means 14 through inlet opening 26. Liquids and solids flow downwardly toward the bottom portion 23 of tank means 10 through discharge opening 22 to form a slurry of water indicated by wave lines and solid particles and dust. The heavier particles will settle toward the bottom of the tank means by gravity. The lighter particles and dust may be carried upwardly with the gas which rises toward the top portion 20 of tank means 10 as bubbles indicated by circles. Wellhead gas under pressure is trapped in chamber 25 and maintains a liquid level in member 21 and members 37 below radial gas discharge inlet openings 35 and adjacent the upper end portions of slots 38 as illustrated by dotted line 41. Tank means 10 is filled with a body of liquids which is primarily water and extends between tank bottom portion 23B and liquid level control means 16 so that hood means 14 is completely immersed in the liquids. A relatively large width annular gas flow channel 42 is provided between the outside of hood cylinder 21 and the inside of the tank wall 43. Gas entrained in the liquids is carried into the body of liquids as liquids are supplied through central main effluent discharge opening 22. Small bubbles of gas are also discharged from chamber 25 into the body of liquids in gas flow channel 42 through circumferentially spaced gas discharge means 34. The small gas bubbles are washed by the water to remove and reduce upward movement of solid particles and dust. In this manner, gas bubbles in the body of liquids continuously rise through the body of liquids toward the gas collection chamber 20 in the upper end portion of tank means 10 while solid particles in the body of liquids continuously descend toward the bottom portion 23B of tank means 10. In order to further reduce upward movement of solid particles and dust, baffle and gas trap means 28 provide a relatively narrow width annular flow channel 44 between annular side wall member 31 and side wall portion 43 of tank means 10. Baffle and gas trap means 28 also provide an annular gas trap chamber 45 which receives upwardly rising gas bubbles and from which gas flows radially outwardly into flow channel 44 through circular openings 32 in annular side wall member 31. In this manner, dust and very fine particles are removed from the gas during flow through circular openings 32 and flow channel 44. The cap member 29 has a conical shape so that any particles carried upwardly beyond flow channel 44 will settle toward the inclined upper surface 46 and move downwardly toward and through flow channel 44.

A slurry solids collection means 50 is mounted below hood means 14 to collect and concentrate solids which are continuously removed as a relatively dilute water-solids slurry through discharge conduit means 52, 54. Collection means 50 is cone shape with an upper annular inlet portion 60 having a relatively large diameter so as to extend radially a substantial distance beyond discharge opening 22 and provide an annular rim portion 61 located closely adjacent tank side wall portion 62. Inlet portion 60 is located directly beneath and in relatively closely spaced axial relationship to hood discharge opening 22 so that most of the solids will descend into and be contained by the collection means 50. An annular relatively small diameter lower discharge portion 64 is connected to discharge pipes 52, 54 by a coupling member 65. In order to remove solid materials which may accumulate in the tank bottom portion 23B, a drain means 66 and a clean-out opening means 67 are provided.

A conventional mist extractor means 70 is located at the top of tank means 10 to remove fine mist droplets of moisture from the gas prior to discharge into a gas outlet line means 72 for delivery to a sales gas line or to additional processing apparatus. In addition, a conventional gas dryer column means 74 may be mounted on the top of tank means 10 to receive some of the gas and to provide a source of control and supply gas for operating various conventional gas operated flow control means as hereinafter explained in detail. The tank means 10 is provided with a conventional relief valve means 75, pressure gauge means 76 and rupture head means 77.

The inlet means 12 is provided with a conventional inlet control valve means 80 and a bypass pipe means 82 with an automatic bypass control means 84. Slurry discharge conduit means 52, 54 have associated conventional automatic control valve means 85, 86 and manual valve means 87, 88. Discharge conduit 66 has a conventional manual control valve means 89. Liquid level control means 16 comprises a float means 90 and conventional level responsive controller unit 91.

In the illustrative embodiment, the automatic control devices are gas operated so as to enable automatic continuous operation at the wellhead site by gas supplied from gas drier means 74 or any other suitable source through a supply line 92 to conventional control gas supply means 93 providing variable pressure control gas to supply lines 94, 95, 96, 97. Control gas supply line means 93 comprises various conventional devices such as a shut-off valve means 100, a strainer means 101, a pressure controller means 102, a flow regulator means 103, a relief valve means 104, a pressure gauge means 105, a drip pot means 106 and a regulator means 107.

In operation, initial separation of effluent components occurs as a result of the change of velocity during discharge into the hood means as well as gravitational forces on the gas, liquids and solids. The effluent comprises gas and solids such as coal (granules, particles and dust), as well as water which is present in a large amount. When the effluent is discharged into the tank means 10 from the hood means 14, most of the solid components thereof are carried downwardly toward the collection means 50. The construction and operation is such that most of the gas is initially collected in the gas trap chamber 25 in the hood means above the water level 41 therebeneath and exits downwardly from the hood means 14 through each of the discharge means 34 whereby the water acts to scrub particles such as fine coal dust from the gas and force its descent to the solids collection means 50. All of the gas rises through the water surrounding the hood means 14 for eventual travel to the top portion of the tank means 10. A substantial portion of the gas rises into the gas trap chamber space 45 under the trap means 28 for final dispersion therefrom through the screen means 31 and upward travel through the water to the upper gas chamber portion 20 of the tank means 10. The cover means 29 of the hood means 14 can be conical so that any solids components which may deposit thereon from the surrounding water will slide off for gravitational travel to the solids collection means 50. The gas in elongated gas chamber 20 travels through the conventional mist extractor means 70 to remove fine droplets of moisture therefrom before being discharged through the gas outlet line means 72. Some of the gas enters the gas dryer column means 74 to provide supply gas for the various gas operated control devices.

The separator apparatus herein described is continuously automatically operable at the wellhead site by pressure of the wellhead effluent and gravity for efficient and effective separation of gas, solids and water contained in natural gas well effluent. Gas operated control means are provided so that the apparatus may be operated by supply gas obtained from the apparatus. The apparatus can operate on a continuous schedule with minimal requirements for monitoring and for down-time maintenance. The solids are removed in a water slurry which may be conveniently discharged to any suitable storage means and the solids may be recovered.

It is to be understood that the above description of a preferred embodiment is meant to be illustrative and not limiting, and that it is intended that the appended claims be construed to include various alternative modifications and embodiments of the invention except insofar as limited by the prior art.

What is claimed is:

1. Apparatus for continuously separating gas, water and solid materials such a coal particles and pieces contained in natural gas well head effluent at a wellhead site comprising:
   a separator tank means mounted in a vertical attitude for continuously receiving a supply of wellhead effluent from the wellhead and having an uppermost gas chamber portion for receiving and holding gas and a lowermost liquid holding portion for holding a confined body of water at a predetermined level therewithin;
   effluent flow control means for controlling the volume of wellhead effluent received in said tank means;
   a hood means mounted in the lowermost liquid holding portion of said separator tank means and being completely immersed in the confined body of water for receiving and separating the wellhead effluent and for providing a gas collection chamber therewithin for containing a body of gas and for continuously downwardly discharging water into the confined body of water below said hood means and maintaining a level of water in the hood means beneath the gas collection chamber in the hood means;
   gas discharge means associated with said hood means for continuously discharging the gas in said gas collection chamber in the hood means into an intermediate portion of the confined body of water and causing the gas to flow upwardly through the confined body of water to said uppermost gas chamber portion of said tank means;
   solids collection means located below said hood means for holding a portion of the confined body of water and collecting solid materials to form a water-solids slurry therewithin;
   slurry outlet means connected to said solids connection means for continuously removing water and solids from said tank means; and
   gas outlet means connected to said uppermost gas chamber portion for continuously removing gas therefrom.

2. The invention as defined in claim 1 and further comprising:
   an annular upwardly extending flow channel means between said hood means and said separator tank means for receiving gas from said gas discharge means.

3. The invention as defined in claim 2 and wherein said hood means comprises:
   an elongated cylindrical member concentrically mounted in said tank means and having a cylindrical side wall spaced from a cylindrical side wall portion of said tank means and defining said annular flow channel means;
   a cylindrical downwardly facing liquid discharge opening at the lower end of said cylindrical member; and
   said gas discharge means being located on said cylindrical member.

4. The invention as defined in claim 3 and further comprising:
   an annular baffle and gas trap means mounted on said hood means for receiving gas bubbles from said flow channel means.

5. The invention as defined in claim and wherein said baffle and gas trap means comprising:
   an annular cover member having a diameter larger than the diameter of said cylindrical member and being mounted at and in upwardly spaced relation to the upper end of said cylindrical member to provide a gas trap chamber between the side wall of said tank means and the side wall of said hood means and a circumferentially spaced radially outwardly extending gas discharge opening means therebetween for discharging gas into said annular flow channel means.

6. The invention as defined in claim 5, and wherein said annular cover member has a conical cross-section configuration.

7. The invention as defined in claims 1 or 6 and wherein said gas discharge means comprises:
   a plurality of circumferentially spaced bubble column means mounted on the periphery of the hood means and having downwardly facing gas discharge openings disposed in the confined body of water between the interior of the side wall of the tank means and the exterior of the side wall of the hood means to disperse relatively small-size gas bubbles and cause downward movement of fine solid particles in said confined body of water.

8. The invention as defined in claim 1 and wherein a mist extractor means is disposed between the gas collection chamber of the upper portion of the tank means and the gas outlet means.

9. The invention as defined in claim 1 and wherein said hood means comprising:
   an elongated cylindrical wall portion mounted coaxially in a lower portion of said separator tank means in circumferentially inwardly spaced relationship with said cylindrical wall portion of said separator tank means to provide an annular upwardly extending first gas passage means therebetween and having a closed upper end portion providing an uppermost gas collection chamber and an open lower end portion providing a downwardly facing effluent discharge opening;

an annular cap means mounted on said upper end portion of said hood means and having a diameter greater than the diameter of said cylindrical wall portion of said hood means and less than the diameter of said cylindrical wall portion of said separator tank means to provide a second annular gas passage therebetween having a lesser width than the width of said first annular gas passage means and to provide a gas trap chamber means above said first annular gas passage means for trapping a portion of the gas rising through said first annular gas passage means and to provide for radial outward flow of gas from said gas trap chamber means into said second annular gas passage means.

10. The invention as defined in claim 9 and wherein:
a lowermost slurry zone of heavyweight particulate material located beneath said effluent discharge opening;
an intermediate slurry zone of intermediate weight particulate material located between said effluent discharge opening and said first primary gas discharge means;
an uppermost slurry zone of lightweight particulate materials located between said first gas discharge means and said second gas discharge means.

11. The invention as defined in claim 9 and wherein said hood means providing:
a lowermost effluent discharge opening means located at a lower end portion for providing a lowermost first large size particle slurry zone;
a first gas flow channel means extending upwardly between said discharge opening means and said cap means for providing an intermediate size slurry and particle zone and for enabling upward movement of gas from said first large particle slurry zone;
an intermediate gas discharge means located between said discharge opening means and said cap means for discharging gas into said first gas flow channel means;
a second gas flow channel means located above said first gas flow channel means between said cap means and said separator tank means and being connected to said first gas flow channel means for receiving upwardly flowing gas therefrom;
gas trap means associated with said cap means for receiving and trapping upwardly flowing gas from said first gas channel means; and
an uppermost gas discharge means associated with said gas trap means for discharging trapped gas into said second gas flow channel means.

12. The invention as defined in claim 1 and wherein said solids collection means comprising:
a cone-shape device having an uppermost inlet opening of larger diameter than the liquid discharge opening of said hood means and being located directly therebelow, and having a lower small diameter discharge opening connected to said slurry outlet means.

13. A method of separating gas, water and solid materials such as coal particles and pieces contained in natural gas wellhead effluent at a wellhead site comprising:
continuously delivering a supply of wellhead effluent to a separator tank means mounted in a vertical attitude;
maintaining a confined body of wellhead effluent in a lower portion of the tank means at an intermediate level in the tank means while collecting gas in a gas collection chamber located in an upper portion of the tank means above the intermediate level of wellhead effluent;
mounting a hood means in the lower portion of the tank means in the confined body of wellhead effluent in radially inwardly spaced relationship relative thereto;
directing the supply of wellhead effluent into the tank means through an upper portion of the hood means and continuously discharging the supply of wellhead effluent into the confined body of wellhead effluent through a downwardly facing effluent discharge opening while trapping a quantity of gas in the hood means to provide a gas trap chamber in the hood means defined by an upper wall and a side wall of the hood means and a level of wellhead effluent in the hood means located above the effluent discharge opening;
continuously discharging the gas trapped in the gas trap chamber in the hood means into the confined body of wellhead effluent and causing the gas to flow upwardly through the confined body of wellhead effluent to the gas collection chamber;
continuously collecting solid materials in a solids collection means in the bottom portion of the tank means below the hood means;
continuously discharging gas from the gas collection chamber for further processing; and
continuously removing water from the tank means through the solids collection means so as to cause removal of solids with the water.

14. The invention as defined in claim 13 and further comprising:
causing the trapped gas to be discharged into the confined body of water at a location above the effluent discharge opening and to flow downwardly into the confined body of wellhead effluent between the hood means and separator tank means.

15. A method of continuously separating gas, water and solid components of natural gas wellhead effluent at a natural gas wellhead site in an elongated vertical cylindrical wall separator tank having a bottom portion and an intermediate portion and upper portion comprising:
placing a cylindrical hood apparatus having an elongated cylindrical side wall and a closed top portion and bottom portion with a downwardly facing lower discharge opening inside a lower portion of the separator tank so as to provide a main annular flow channel between the cylindrical side wall of the hood apparatus and the cylindrical wall of the separator tank and a liquid holding chamber beneath the hood apparatus;
filling the lower portion and the intermediate portion of the tank with water so as to provide a body of water to completely immerse the outer surface of the cylindrical hood apparatus and provide an upper level of water located above the hood apparatus and below the top portion of the separator tank and to provide an uppermost gas chamber between the upper level of water and the top portion of the separator tank;
discharging the wellhead effluent directly into the hood apparatus through an inlet opening located in the cylindrical side wall between the closed top portion and the discharge opening;
separating the gas from the water and solid materials in the hood apparatus and collecting a primary body of gas in an upper portion of the hood apparatus while discharging the water and solid materials downwardly toward the bottom portion of the separator tank;

moving the solid materials downwardly in the body of water toward the bottom of the separator tank to form a water and solids slurry therein;

maintaining an upper level of water within a lower portion of the cylindrical side wall of the hood apparatus above said discharge opening by pressure of the main body of gas collected in the upper portion of the hood apparatus;

discharging gas into the body of water from the body of gas collected in the hood apparatus through gas outlet devices having discharge openings located in the annular flow channel between the cylindrical side wall of the hood apparatus and the wall of the separator tank and forming gas bubbles in the body of water in the annular flow channel and moving the gas bubbles upwardly through the water in the main annular flow channel toward and into the uppermost gas chamber in the upper portion of the separator tank; and continuously removing gas from the uppermost chamber in the upper portion of the separator tank and continuously removing water and solid materials from the bottom portion of the separator tank.

16. The method as defined in claim 14 and further comprising:

mounting baffle and gas trap apparatus on the upper end portion of the hood apparatus to provide a second annular flow channel having a lesser width than the main annular flow channel;

collecting a secondary body of gas in the baffle and gas trap apparatus from gas bubbles moving upwardly in the main annular flow channel; and discharging gas from the secondary body of gas into the second annular flow channel.

* * * * *